United States Patent
Pong

[11] Patent Number: 5,833,637
[45] Date of Patent: Nov. 10, 1998

[54] REPELLANT TUBULAR CAST FOR IMMOBILING A BODY PART

[75] Inventor: Henry Pong, West Palm Beach, Fla.

[73] Assignee: Biofab, Inc., West Palm Beach, Fla.

[21] Appl. No.: 757,433

[22] Filed: Nov. 27, 1996

Related U.S. Application Data

[63] Continuation of Ser. No. 344,484, Nov. 21, 1994, abandoned, which is a continuation of Ser. No. 49,532, Apr. 20, 1993, abandoned.

[51] Int. Cl.⁶ .......................................... A61F 5/00
[52] U.S. Cl. .................................. 602/5; 602/7; 602/58
[58] Field of Search .................... 602/1, 3, 5, 6, 602/8, 20, 21, 41, 42, 57, 58, 63

[56] References Cited

U.S. PATENT DOCUMENTS

| | | | |
|---|---|---|---|
| 4,948,651 | 8/1990 | DeBusk et al. | 602/43 |
| 5,454,780 | 10/1995 | Duback et al. | 2/6 |
| 5,520,621 | 5/1996 | Edenbaum et al. | 602/6 |

*Primary Examiner*—Wynn Wood Coggins
*Assistant Examiner*—A. Nguyen
*Attorney, Agent, or Firm*—McHale & Slavin PA

[57] ABSTRACT

A cast is disclosed comprising a membrane, padding and immobilizing material. The membrane repels water but allows oxygen and vapor to pass outwardly from the skin. The padding is disposed between the membrane and immobilizing material. The membrane prevents the wet padding from direct contact with the wearer's skin.

9 Claims, 5 Drawing Sheets

REPELLANT TUBULAR CAST FOR IMMOBILING A BODY PART

This is a continuation of Ser. No. 08/344,484 having a filing date Nov. 21, 1994, now abandoned, which is a continuation of Ser. No. 08/049,532 having a filing date Apr. 20, 1993, now abandoned.

BACKGROUND OF THE INVENTION

1. Field of the Invention

The present invention relates generally to a tubular cast material and more particularly to a tubular cast material that is waterproof yet able to allow vapor and oxygen to pass through.

2. Background of the Invention

Fiberglass has taken the place of plaster of paris for use as an immobilizing material, i.e. cast. Typically the cast is applied on top of padding. The padding can be constructed from numerous materials, i.e. cotton, polyester, etc. A wearer of such cast and padding must avoid water or other liquids, as the padding underneath the cast is known to remain wet or damp for many hours after the initial contact with the liquid. After several hours of exposing the wearer's skin to the wet padding, skin maceration, chemical dermatitis, infections, as well as other irritations, to the skin have been commonly known to occur.

To avoid the above-identified problem, the prior art has attempted to develop ways of preventing the padding from becoming wet when the wearer is exposed to some form of liquid. One example of such attempts is U.S. Pat. No. 5,102,711 issued to Keller et al. in which the padding is provided between a top and bottom layer comprising a sheet of porous water impermeable, moisture-vapor-permeable film bonded to the middle layer.

It is, therefore, to the effective resolution of the aforementioned problems and shortcomings that the present invention is directed.

SUMMARY OF THE INVENTION

The present invention provides a tubular conformable, waterproof, breathable membrane which allows moisture protection for the skin and soft tissue and used in conjunction with a fiberglass cast which includes cast padding. This invention enables the user to have an easier application with the cast and provides greater protection against cast saw abrasions and cuts than previous water proof casting materials. Additionally, the present invention provides further protective defense when removing the cast to insure less cuts and abrasions from the oscillating saw.

The present invention includes a tubular membrane stocking, which enables moisture to vaporize from the skin after repeated liquid exposures. The membrane is waterproof, yet able to let vapor and oxygen to pass through outwardly. The membrane does not have any pores. As such, no clogging or leaking can occur.

The membrane repels water due to the fact that the water molecules are strongly attached to each other, thus forming a single molecule. Since the water molecules are attached to each other to form a single molecule they cannot attach to the positive and negative charges of the molecular chains within the membrane. Thus, the hydrophobic membrane literally repels water.

However, vapor is allowed to pass through the membrane since the vapor molecules are very independent from each other and move rather freely, similar to a cloud. Thus, the vapor molecules behave very differently from water molecules. As the vapor molecules are not attached to each other, they are able to attach to other molecules. The individual vapor molecules are attracted to the membrane by attaching themselves to the negative and positive charges within the membrane and are passed through the membrane from one side to another outwardly from the skin. The direction the vapor molecules travel within the membrane depends on the number of vapor molecules on each side. Additionally, the absolute number of vapor molecules depends on the temperature and relative humidity. As vapor molecules try to escape from the moister area, the vapor molecules will travel from inside the garment to the outside.

The stocking is thin which provides a less bulky application enabling surgeons and technicians to conform their casts which insures better immobilization of fractures and soft tissue injuries.

The stocking provides a waterproof liner and allows a physician or orthopedic technician to use the membrane stocking in combination with other cast paddings to provide adequate protection of bony prominences and soft tissue lesions. Thus, giving the surgeon or cast applicant a broad degree of thickness and conformity for controlled immobilization.

The membrane is non-porous and has no micropores that could clog with salt, dirt, or oil. Its waterproof properties are unaffected, even under severe condition, i.e. when the membrane is exposed to salt water.

The present invention uses the above-described membrane stocking in conjunction with a fiberglass cast and cast padding. When used in conjunction with a cast, the membrane allows for the evaporation of perspiration, enhancing comfort for the wearer and decreasing the associated odor producing problems commonly associated with conventional casting.

The present invention allows for an easier application by a physician or technician as compared to the prior art. The present invention is less bulky than the prior art and provides for better conformability to the casted extremity. By being less bulky, the present invention allows for proper setting of the bones. Furthermore, no overlapping or doubling of layers is needed and there are no open seams. There is no danger of burning the patients skin when removing the cast by a cast saw as the membrane gives with the cast saw. Finally, the present invention provides for a better fit under the patients clothing.

Thus, it is the primary object of the present invention to provide a tubular membrane for use in conjunction with a conventional cast which is waterproof yet breathable, keeping the skin dry at all times.

It is another object of the present invention to provide a tubular membrane for use in conjunction with a conventional cast which will allow for the evaporation of perspiration.

It is a further object of the present invention to provide a tubular membrane for use in conjunction with a conventional cast which will prevent the cast padding from being in direct contact with the wearer's skin, thus preventing skin maceration and chemical irritation.

It is yet another object of the present invention to provide a tubular membrane for use in conjunction with a conventional cast which will allow for better immobilization of fractures and soft tissue injuries.

It is still another object of the present invention to provide a tubular membrane for use in conjunction with a conventional cast which provides for greater protection against cast saw abrasions, cuts and burns at time of removal.

It is even still another object of the present invention to provide a tubular membrane for use in conjunction with a conventional cast which is cuffable.

It is even further another object of the present invention to provide a tubular membrane for use in conjunction with a conventional cast which decreases the odor producing problems associated with casting for extend periods.

Other objects and advantages of this invention will become apparent from the following description taken in conjunction with the accompanying drawings wherein set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

The invention may be better understood by reference to the drawings in which.

DETAILED DESCRIPTION OF THE PREFERRED EMBODIMENT

Figure 1:
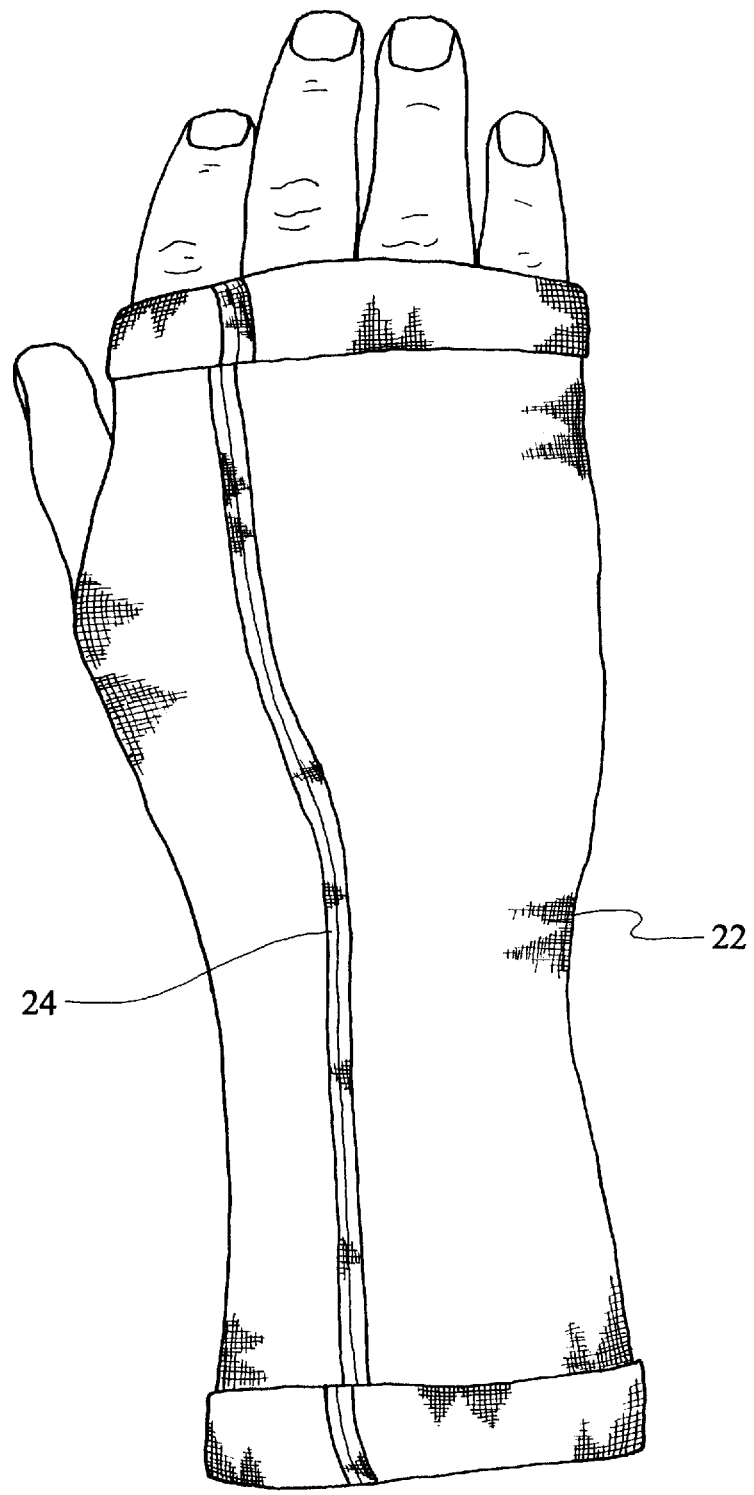
FIG. 1 is a perspective view showing the laminated membrane fitted onto a human arm.
Figure 2:
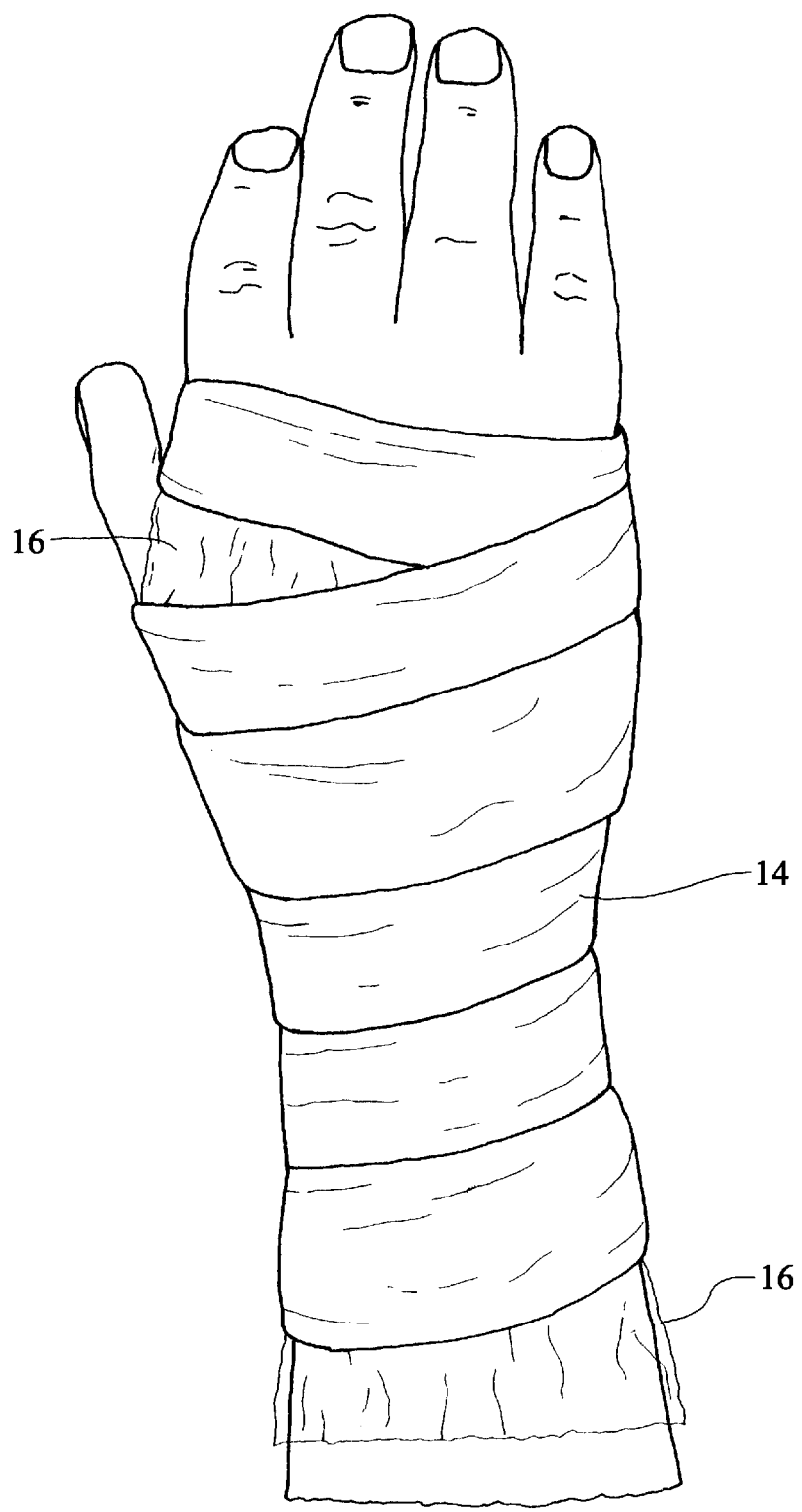
FIG. 2 is a perspective view showing the cast padding wrapped around the laminated membrane of FIG. 1.
Figure 3:
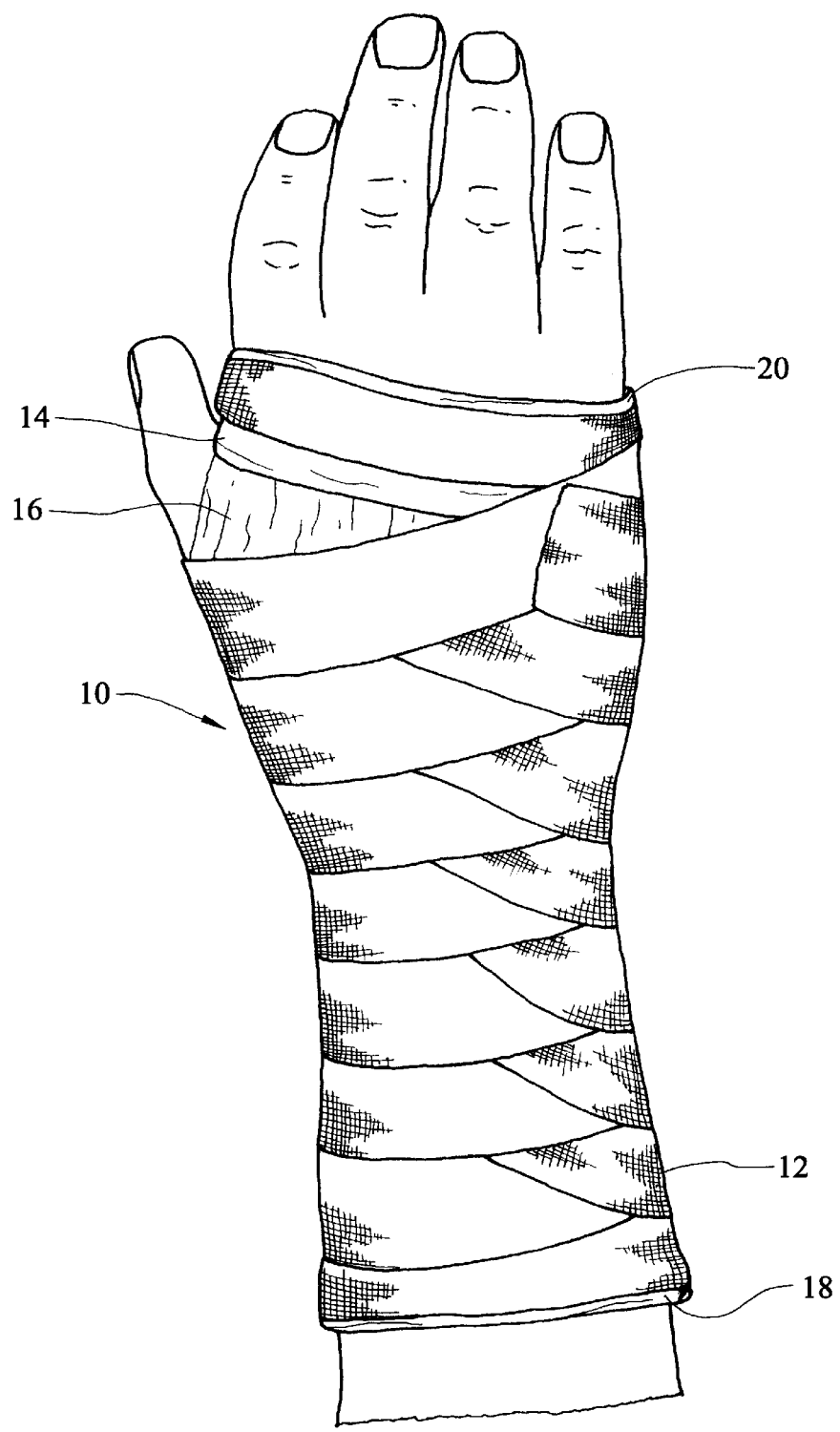
FIG. 3 is a perspective view showing the present invention in use on a human arm.
Figure 4:
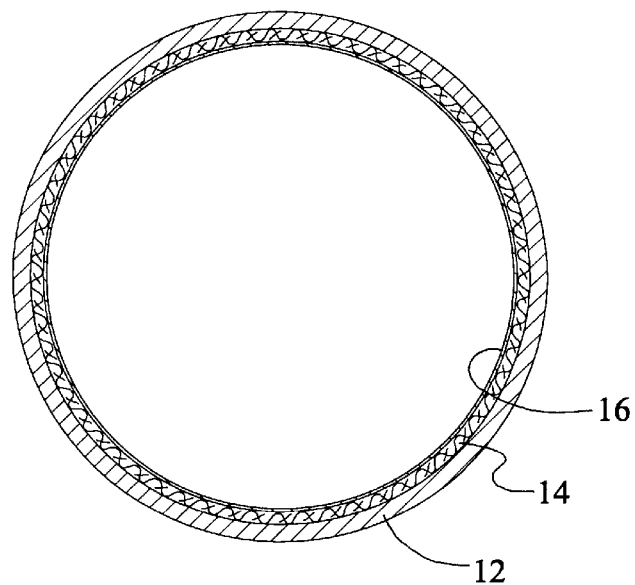
FIG. 4 is a cross sectional view of the present invention.
Figure 6:
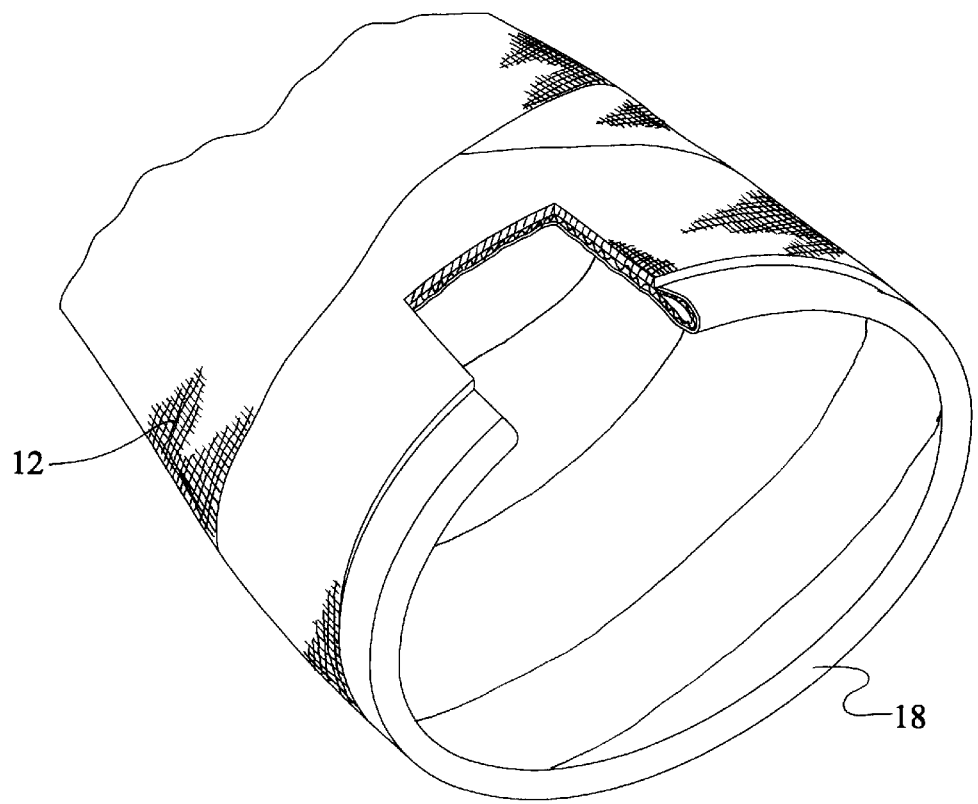
FIG. 6 is a perspective view showing the edge portion of the present invention.

Now referring to the drawings, the first embodiment of the present invention is shown at 10 and generally includes a cast or immobilizing material 12, cast padding 14 and tubular membrane 16. Tubular membrane 16 is waterproof but allows vapor and moisture to pass through. Thus, tubular membrane 16 allows perspiration to evaporate which reduces odors emanating from within the cast.

Figure 5:
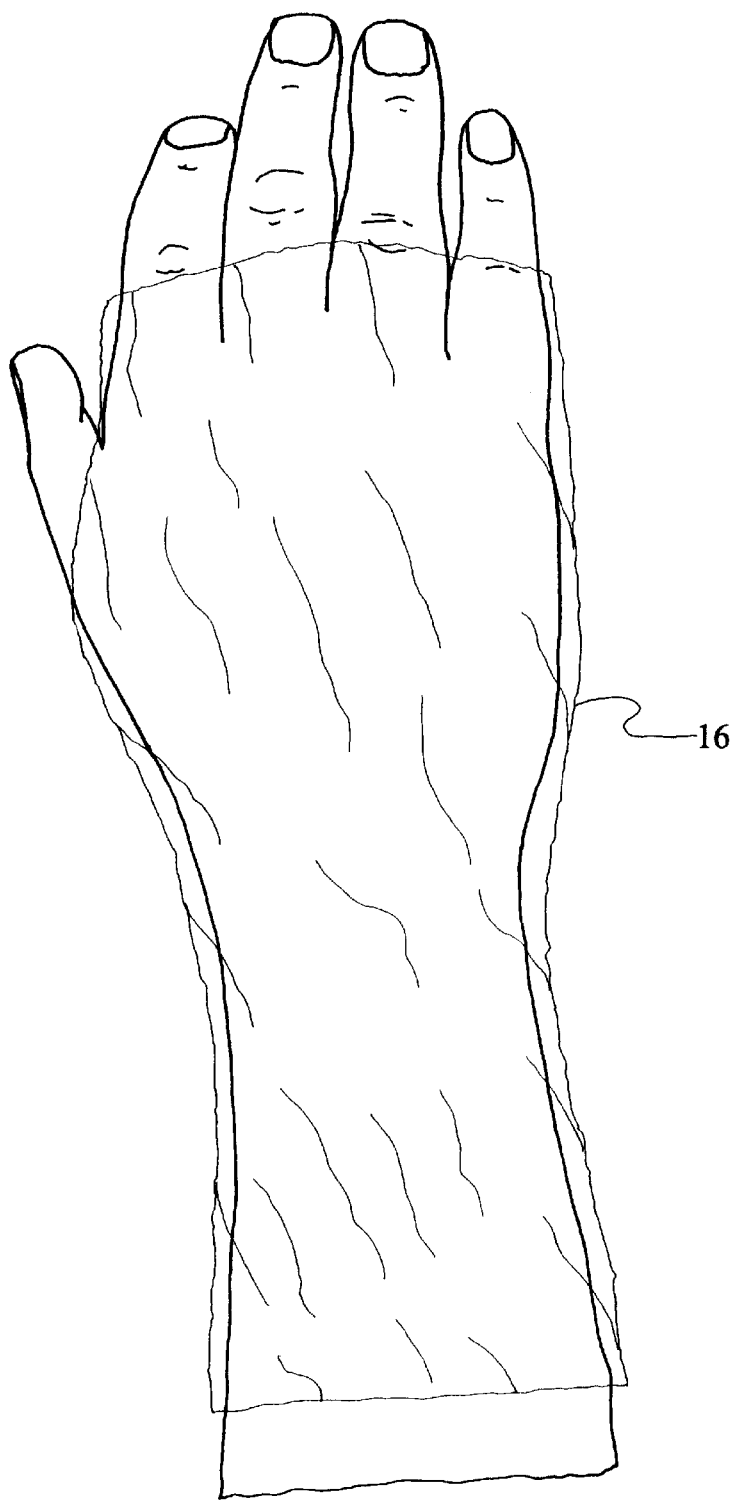
FIG. 5 is a perspective view showing the membrane fitted onto a human arm.

In this first embodiment, a cloth or fabric 22, such as polyester or the like, is laminated to one side of the tubular membrane 16. Fabric 22 provides a stretchable backing to the membrane for excellent conformability. In the second embodiment (FIG. 5) the tubular membrane 16 is shown without cloth 22. In either embodiment, all of the advantages and unique features of the present invention are achieved. However, the cloth 22 provides extra strength and reinforcement to the tubular membrane 16 and helps in preventing membrane 16 from tearing.

Preferably, tubular membrane 16 is constructed from a hydrophilic polyester block copolymer and is a homogeneous, non-porous flat film. Membrane 16 obtains its tubular form by providing a single flat waterproof seam 24. Membrane 16 provides comfort and coolness to the wearer and prevents the wearer's skin from being irritated by the garment material of padding 14. Membrane 16 is waterproof and provides moisture protection for the wearer's skin and soft tissue. Membrane 16 provides greater protection against cast saw abrasions and cuts over previous casts. Membrane 16 enables moisture to vaporize from the wearer's skin after repeated liquid exposures. Membrane 16 is very thin, thus, less bulky for allowing physicians, technicians or trainers to more accurately conform the cast/garment for insuring better immobilization of fractures and soft tissue injuries.

Membrane 16 repels water, as well as other liquids, due to the fact that the water molecules are strongly attached to each other, thus forming a single molecule. Since the water molecules are attached to each other'to form a single molecule they cannot attach to the positive and negative charges of the molecular chains within membrane 16. Thus, membrane 16 literally repels water and liquids from contacting the skin. It is a semipermeable biologic membrane and not just a finely porous barrier.

Vapor is allowed to pass through membrane 16 since the vapor molecules are very independent from each other and move rather freely. Thus, the vapor molecules behave very differently from water molecules. As the vapor molecules are not attached to each other, they are able to attach to other molecules. The individual vapor molecules are attracted to membrane 16 by attaching themselves to the negative and positive charges within membrane 16 and are passed through membrane 16 from one side to another, outwardly from the skin. The direction the vapor molecules travel within membrane 16 depends on the number of vapor molecules on each side. Additionally, the absolute number of vapor molecules depends on the temperature and relative humidity. As vapor molecules try to escape from the moister area, the vapor molecules will travel from inside the garment to the outside.

In application, the tubular membrane 16 is gloved around the body portion which is to be immobilized. Cast padding 14 can be constructed from either cotton, polyester, foam or the like. Cast padding 14 is then wrapped around a majority of membrane 16 except the first and second ends of membrane 16. Once padding 14 is wrapped around membrane 16 the first and second ends of membrane 16 are folded over cast padding 14 to provide first and second edges 18 and 20, respectively. Lastly the immobilizing material (cast 12) is applied around cast padding 14 and cuffed edges 18 and 20. Cuffed edges 18 and 20 are attached to inside of cast 12, by bonding, sealing or the like, to completely seal cast padding 14 from water as well as other liquids. Additionally, cuffed edges 18 and 20 prevent the usual unravelling problems after long term usage often associated with conventional casts. In the event that cast padding 14 does get wet, membrane 16 prevents the wet padding from being directly in contact with the wearer's skin. The present invention allows for post-operation hydro therapy with a whirlpool for upper and lower extremity as well as allowing the wearer to perform other activities which might cause the cast to become wet. In fact, swimming, showering and bathing are possible and encouraged for quicker recovery.

Though the present invention is only shown in use in conjunction with a human arm, it is to be understood that the present invention can be utilized on various other body parts. Other uses of the material can be expanded to provide the same skin protective advantages described above for application under braces, splints, stockings for amputated limbs, etc. In different sizes and shapes it can be used for protective footwear, caps and gowns used in the operating room or other medical settings.

It is to be understood that while I have illustrated and described certain forms of my invention, it is not to be limited to the specific forms or arrangement of parts herein described and shown. It will be apparent to those skilled in the art that various changes may be made without departing from the scope and advantages of the invention and the invention is not to be considered limited to what is shown in the drawings and described in the specification.

What is claimed is:

1. A cast for immobilizing a body part, comprising:
   a single layer, tubular membrane constructed from polyester block copolymer and characterized by the ability to repel liquid water and allow vapor and oxygen to pass through outwardly, said membrane having a first surface and a second surface, said first surface of said membrane adapted to abut the body part to be immobilized;
   a fabric member laminated to said second surface of said membrane, said fabric member for providing strength and reinforcement to said membrane;
   a padding member for covering the body part to be immobilized; and
   an immobilizing material for immobilizing the body part to be immobilized, said immobilizing material operatively associated with said padding member and said membrane, said padding member disposed between said membrane and said immobilizing material.

2. The cast of claim 1, wherein said padding member having a first surface and a second surface, said padding member and said membrane each having a first end and a second end.

3. The cast of claim 2, wherein said first surface of said membrane is adapted to be disposed about the body part to be immobilized.

4. The cast of claim 2, wherein said first surface of said padding member is disposed around said membrane except near said first and second ends of said membrane to allow said first and seconds of said membrane to be folded over said first and seconds of said padding, respectively.

5. The cast of claim 2, wherein a portion of said membrane is attached to said first surface of said immobilizing material.

6. A cast for immobilizing a body part, comprising:
   a single layer membrane constructed from a polyester block copolymer tubular membrane and characterized by the ability to repel liquid water and allow vapor and oxygen to pass through, said tubular membrane adapted to be disposed about the body part to be immobilized, said tubular membrane having a first end, and a middle portion, a second end, and a first surface and a second surface, said first surface of said tubular membrane adapted to abut the body part to be immobilized;
   a fabric member laminated to said second surface of said tubular membrane, said fabric member providing strength and reinforcement to said tubular membrane;
   a padding member having a first surface and a second surface, said first surface of said padding member placed around said middle portion of said membrane to allow said first and second ends of said membrane to be folded over said padding; and
   an immobilizing material operatively associated with said padding member and said membrane, said padding member disposed between said fabric member and said immobilizing material.

7. The cast of claim 6, wherein a portion of said membrane is secured to said first surface of said immobilizing material.

8. A cast for immobilizing a body part, comprising:
   a single layer, constructed from a polyester block copolymer tubular membrane and characterized by the ability to repel liquid water and allow vapor and oxygen to pass through, said tubular membrane adapted to be disposed about the body part to be immobilized, said tubular membrane having a first end, a middle portion, a second end, and a first surface and a second surface, said first surface of said tubular membrane adapted to abut the body part to be immobilized;
   a fabric member laminated to said second surface of said membrane, said fabric member for providing strength and reinforcement to said membrane;
   a padding member having a first surface and a second surface, said first surface of said padding member placed around said middle portion of said membrane to allow said first and second ends of said membrane to be folded over said padding; and
   an immobilizing material operatively associated with said padding member and said membrane, said padding member disposed between said fabric member and said immobilizing material by use of cuffed edges to seal said padding between said membrane and an outer surface of said immobilizing material.

9. The cast of claim 8, wherein a portion of said membrane is attached to said first surface of said immobilizing material.

* * * * *